United States Patent
Nikolic et al.

[11] Patent Number: 5,962,547
[45] Date of Patent: Oct. 5, 1999

[54] REACTIVE RADIATION- OR THERMALLY-INITIATED CATIONICALLY-CURABLE EPOXIDE MONOMERS AND COMPOSITIONS MADE FROM THOSE MONOMERS

[76] Inventors: Nikola A. Nikolic, 362 Burdock Ct., Three Bridges, N.J. 08887; Rose Ann Schultz, Rd. #1 Sunset Ave., Box 431, Princeton, N.J. 08540

[21] Appl. No.: 09/078,768

[22] Filed: May 14, 1998

Related U.S. Application Data

[63] Continuation-in-part of application No. 08/857,667, May 16, 1997, abandoned.

[51] Int. Cl.$^6$ ............................................. C08F 2/46
[52] U.S. Cl. ...................... 522/170; 522/8; 522/9; 522/10; 522/25; 522/63; 522/64; 522/65; 522/66; 522/68; 522/90; 522/97; 522/98; 528/408; 528/406; 528/405; 528/73
[58] Field of Search ............................. 522/8, 9, 10, 25, 522/50, 55, 63, 64, 65, 66, 68, 90, 97, 98, 170; 528/73, 405, 406, 408

[56] References Cited

U.S. PATENT DOCUMENTS

| | | | |
|---|---|---|---|
| 3,455,967 | 7/1969 | Hatch | 260/348 |
| 3,506,612 | 4/1970 | Neville et al. | 260/47 |
| 3,634,523 | 1/1972 | Lund et al. | 260/618 D |
| 3,635,843 | 1/1972 | Parry et al. | 260/2 N |
| 4,058,401 | 11/1977 | Crivello | 96/115 R |
| 4,069,055 | 1/1978 | Crivello | 96/115 R |
| 4,096,154 | 6/1978 | Rempfler et al. | 260/327 |
| 4,216,288 | 8/1980 | Crivello | 430/280 |
| 4,256,828 | 3/1981 | Smith | 430/280 |
| 4,731,428 | 3/1988 | Waterman | 528/69 |
| 4,764,581 | 8/1988 | Muller et al. | 528/100 |
| 5,086,189 | 2/1992 | Lecloux et al. | 549/531 |
| 5,118,822 | 6/1992 | Shum et al. | 549/529 |

FOREIGN PATENT DOCUMENTS

| | | | |
|---|---|---|---|
| 0252358 | 6/1987 | European Pat. Off. | C07D 303/24 |
| 0 763 555 | 3/1997 | European Pat. Off. | C08G 65/26 |
| 4340949 | 6/1995 | Germany | C08L 63/00 |
| 19534594 | 3/1997 | Germany | C08L 63/00 |
| 19534668 | 3/1997 | Germany | C08L 63/00 |
| 2012780 | 1/1979 | United Kingdom | C08G 75/02 |
| WO 95/21207 | 8/1995 | WIPO | C08G 59/22 |
| WO 96/13538 | 5/1996 | WIPO | C08G 59/68 |
| WO 97/21229 | 6/1997 | WIPO | H01B 1/22 |

OTHER PUBLICATIONS

Jones, Richard G. et al., Radiation chemistry and the lithographic performance of chemical amplification resist formulated from poly (4)epoxystyrene–star–styrene) and a photoacid generator.J.Mater.Chem., 1997, 7(3), 421–427.
Murphy, J.J. et al., "Electron beam resists based on oxirane functionalised polystyrenes." Microelectronic Engineering 35 (1997) 121–124.
Reets, Ivo et al., "Thermally induced radical promoted cationic polymerization using a novel N–allyloxy–pyridinium salt." Macromol.Chem.Phys. 198, 19–28 (1997).
Crivello, J.V. "Cationic Polymerization— Iodonium and Sulfonium Salt Photoinitiators", Adv. Polym. Sci., 1984, 62 1–48.
Corey, Paul F. et al., Buffered Potassium Peroxymonosulfate–Acetone Epoxidation of α,β–Unsaturated Acids, J. Org. Chem. 1986, 51, 1925–1926.
Crivello J.V. et al., "Diaryliodonium Salts as Thermal Initiators of Cationic Polymerization", J. of Poly. Sci., vol. 21, 97–109 (1983).
Abdul–Rasoul, Firas et al, "Photochemical and thermal cationic polymerizations promoted by free radical initiators", Polymer, 1978, vol. 19, Oct., pp. 1219–1223.
Yang, D. Billy et al., "Inorganic and Organometallic Photoinitiators", Radiation Curing: Science and Technology, edited by S. Peter Pappas, Plenum Press, New York, 1992.
Crivello, J. V. et al., "Novel Epoxynorbornane Monomers. 1: Synthesis and Characterization", Macromolecules 1996, 29, 433–438.
Crivello, J.V. et al., "Novel Epoxynorbornane Monomers. 2: Cationic Photopolymerization", Macromolecules 1996, 29, 439–445.
Priou, C. et al., "Cationic phogopolymerizatin of epoxy modified silicones for application to silicone release papers" A new photoinitiator, J. Coatings Technology, vol. 67, No. 851, Dec. 1995, pp. 71–78.
Crivello, J.V. et al., "Studies of synthesis and cationic photopolymerization of three isomeric monoterpene diepoxides", J. Polymer Science: Part A: Polymer Chemistry, vol. 33, 1881–1890 (1995).
Hacker, Nigel P., "New Reactions of Cationic Photoinitiators" pp. 473–504.
Crivello, J.V., "Latest Developments in the Chemistry of Onium Salts", pp. 435–471.
Carter, J. Wells et al., "Formulation variables affecting extractables in cationic, UV–cured, epoxide coatings", Water–Borne, Higher–Solids and Powder Coatings Symposium, Feb. 26–28, 1992, New Orleand, LA, pp. 421–430.

(List continued on next page.)

*Primary Examiner*—Frederick Krass

[57] ABSTRACT

Radiation- or thermally-initiated cationically-curable styrene oxides of the structure

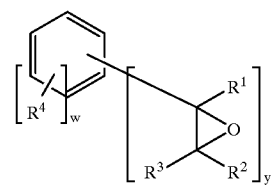

are suitable for use in cationically curable adhesive and coating compositions.

4 Claims, 1 Drawing Sheet

OTHER PUBLICATIONS

"Urethane Polymers", Encyclopedia of Chemical Technology, 4th ed. vol. 24, pp. 723–726.

Herweh, John E. et al., "Photodegradation of Some Alkyl N–Arylcarbamates", J. Org. Chem. 1980, 45, 2195–2201.

Decker, C. et al., "Photodegradation of UV–cured Coatings, II. Polyurethane–Acrylate Networks" J. Polymer Science: Part A: Polymer Chemistry, vol. 29, 739–747 (1991).

Rek, Vesna, "Photodegradation of Polyurethanes", pp. 134–165.

REACTIVE RADIATION- OR THERMALLY-INITIATED CATIONICALLY-CURABLE EPOXIDE MONOMERS AND COMPOSITIONS MADE FROM THOSE MONOMERS

This application is a continuation-in-part of application Ser. No. 08/857,667, filed May 16, 1997, now abandoned.

FIELD OF THE INVENTION

This invention relates to radiation- or thermally-initiated, cationically-curable epoxides and adhesives or coatings compositions comprising those epoxides.

BACKGROUND OF THE INVENTION

Electron-beam and UV-cured adhesives are currently the most rapidly growing segments of the radiation-cured polymer market. Of particular commercial importance are UV-curable epoxide adhesive formulations, which typically consist of three principle components: i) cationic photoinitiators, ii) alcohols or polyols, and iii) epoxide monomers.

The photoinitiators are chemically-inert compounds that liberate acidic species upon exposure to actinic radiation. These acidic species then catalyze the crosslinking of the epoxide monomers. Typical photoinitiators include diaryliodonium, triarylsulfonium and ferrocenium salts.

Alternatively, it is possible to thermally initiate cure through the use of those onium or pyridinium salts that are known to afford cationic species capable of initiating cationic cure upon heating. For example, it is known that N-benzylpyridinium and related quaternary ammonium salts afford acidic species under thermolysis conditions (Lee, S. B.; Takata, T.; Endo, T., *Macromolecules*, 1991, 24, 2689–2693). It is also known that diaryliodonium salts thermally decompose in the presence of catalytic amounts of copper compounds (Crivello, J. V.; Lockhart, R. T. P.; Lee, J. L., *J. Polym. Sci., Polym. Chem. Ed.* 1983, 21, 97), and that these diaryliodonium salts can be converted to acidic species via decomposition of benzpinacol (Abdul-Rasoul, F. A. M.; Ledwith, A.; Yagci, Y. *Polymer*, 1978, 19, 1219–1223), or peroxides (Crivello, J. V.; Lam, J. H. W. *Polym. Photochem.* 1982, 2, 219). A recent report indicates that N-allyloxypyridinium salts can be thermally converted to acidic species in the presence of 2,2'-azobutyronitrile or benzoyl peroxide (Reetz, I.; Bacak, V.; Yagci, Y. *Macromol. Chem. Phys.* 1997, 98, 19–28). Any of these routes will liberate cationic species capable of effecting the ring-opening polymerization of the styrene oxides.

The alcohols or polyols act as a source of active protons, thereby facilitating the conversion of the photoinitiator to the cationic species, which activates the cationic polymerization. They also provide flexibility and impact resistance to the formulation through copolymerization with the epoxides.

The epoxide monomers used in these formulations are mainly cycloaliphatic epoxides, although glycidyl esters, glycidyl ethers and epoxidized alpha-olefins also have been used. The cycloaliphatic epoxides are the preferred compounds because they are more reactive than epoxides of straight chain aliphatics. It has been surmised that this greater reactivity is the result of two structural features: cleavage of either C—O bond leads to formation of a relatively stable secondary carbocation; and the cleavage of a C—O bond also releases the ring-strain associated with the bicyclic ring fusion.

The most common epoxide resin in UV-curable formulations is a bis-cyclohexene oxide (available from Union Carbide, product ERL-4221) connected by an ester group. This bis-cyclohexene oxide possesses sufficient reactivity to provide good crosslinking at ambient temperature. Moreover, the ester group is the only other functionality present and it is transparent to UV-radiation. However, there are drawbacks to this monomer. The bis-epoxide is an inherently non-flexible material and consequently produces a brittle crosslinked network. Such brittle materials are susceptible to mechanical stresses in manufacturing operations or end use applications. To counteract this, the epoxide can be co-reacted with one or more flexible diols in order to provide needed flexibility. However, the cycloaliphatic epoxides are not compatible with a particularly broad range of diols, which consequently limits the range of properties that may ultimately be achieved.

Although Crivello, et al. (*Radiation Curing in Polymer Science and Technology*, Vol.2, J. P. Fouassier and J. F. Rabek (Eds.), Elsevier Applied Science, New York, 1993, pp 435–472; *Macromolecules*, 1996, 29, 433–438 and 439–445; *J. Polym. Sci., Polym. Chem.* 1995, 33, 1881–1890) have reported several epoxide structures (e.g., epoxy norbornene and limonene oxides) that reputedly overcome some of the drawbacks of traditional cyclohexene oxides, there is a need for new monomers that are cationically curable and that avoid the problems of the cycloaliphatic epoxide monomers.

SUMMARY OF THE INVENTION

This invention comprises radiation- or thermally-initiated cationically-curable compounds containing a styrene oxide moiety of the structure:

in which $R^1$ to $R^4$ independently represent hydrogen, or aliphatic, alicyclic or aromatic groups, which may contain heteroatoms, characterized in that they do not hinder the cationic polymerization of the epoxy functionality either through steric interaction or through the action of a Lewis base; y is an integer 1–6, w is an integer 0–5, provided that $y+w \leq 6$.

Examples of representative styrene oxides, but not intended as a limitation, are those derived from styrene, isoeugenol, or cinnamyl alcohol, such as those having the structures here:

in which n is the integer 0 to 5 in which R' is —H, —OCH₃, —O—C(O)CH₃;

in which R is —OCH₃, or —OC(O)CH₃

The epoxidation may be performed on the starting olefinic compound by any suitable method known in the art, but is preferably conducted through a potassium monopersulfate/acetone oxidation of the olefinic portion of the corresponding styrene. The styrene compound is suspended in a mixture of acetone and water, and buffered with sodium bicarbonate, which serves to prevent decomposition of the resultant oxides. This suspension is then treated with an excess of the oxidant, provided as an aqueous solution of the monopersulfate compound $(2KHSO_5 \cdot KHSO_4 \cdot K_2SO_4,)$ (Oxone®, a product of DuPont). The recovered solution is partitioned with ethyl acetate, toluene, methylene chloride, or other suitable solvent. Workup consists of washing the organic layer with water followed by drying with a non-acidic drying agent (e.g., anhydrous sodium bicarbonate). Filtering this mixture, followed by removal of organic solvent in vacuo, affords the desired epoxide in high yield without further purification. The resultant epoxides are stable indefinitely at room temperature, provided no acidic components are present.

There are a number of advantages to this procedure. The process is inexpensive and is suitable for scale-up. The reagents involved (i.e. Oxone® monopersulfate, acetone, sodium bicarbonate and ethyl acetate) are relatively innocuous, and all of these materials are non-halogenated. No significant exotherms (change in temperature <10° C.) are noted during the epoxidations, and it is believed that the reaction mixture is not inherently flammable. The process affords the desired product in high yield without a purification step; and the product obtained is of high purity (>95% by $^1$H NMR). The products obtained by this procedure demonstrate low total chlorine content (<30 ppm), which makes them likely candidates for electronics applications. Finally, the pH of the reaction and workup is essentially neutral, thereby precluding premature advancing of the epoxide by adventitious acid. This is a distinct advantage over the peracid epoxidations described in the literature, which generate by-products that cause the styrene oxide products to degrade.

These styrene oxides are eminently suitable for use in radiation- or thermal initiated cationically-curable compositions for several reasons. They are extremely reactive crosslinking agents, curing at room temperature, and they polymerize faster than analogous compositions containing cycloaliphatic epoxides. This faster cure speed implies faster processing speeds for end users, and the higher reactivity translates into formulations that require decreased amounts of monomer while delivering identical rates and extents of cure.

For cycloaliphatic epoxides, such as those derived from cyclohexene oxide, and typical photoinitiators, it has been surmised that moisture may slow the cure rate by reacting with the superacid initiating species (e.g., $HSbF_6$, which would be derived from $Ar_3S^+SbF_6^-$, a typical photoinitiator) to form a hydronium ion and a counterion. The hydronium ion is not sufficiently acidic to react with the cycloalipatic epoxide and continue the crosslinking.

In contrast, the epoxy functionality of the styrene oxide monomers is more easily ring-opened to form the benzylic carbocation in the presence of either a superacid or a hydronium ion, and consequently the polymerization is continued and not terminated by the reaction of the initiating species with moisture. Furthermore, the longer lifetime of the benzylic carbocation permits cure to continue even after exposure to the actinic radiation is ceased, and may allow for curing in regions that were not directly exposed to the actinic radiation, so-called dark curing.

In addition, these monomers contain an aromatic chromophore that absorbs actinic energy at wavelengths other than the wavelengths that activate the photoinitiators. This absorption promotes the monomers to an excited state and results in increased reactivity. This aromatic benefit is not possible in cycloaliphatic epoxides, which do not possess chromophore substituents. It was unexpected that the absorption of energy by the chromophore would not hinder the reactivity of these compounds.

The enhanced reactivity of these monomers allows for formulation with a wider variety of alcohols or polyols, which may also contain other functionalities, leading to differentiated products and formulations. In addition to acting as a source of active protons and thereby facilitating the conversion of the photoinitiator to the acidic species, the alcohols and polyols provide flexibility and impact resistance to the formulation through copolymerization with the epoxides.

Thus, in another embodiment, this invention is an adhesives or coating composition containing one or more styrene oxide monomers as described herein, a photo- or thermal-initiator, and optionally, one or more alcohols or polyols.

Suitable photoinitiators include those diaryliodonium, triarylsulfonium and ferrocenium salts that are known to initiate cationic cure. Suitable thermal initiators are those onium or pyridinium salts that are known to afford cationic species capable of initiating cationic cure upon heating. For example, N-benzylpyridinium and related quaternary ammonium salts, diaryliodonium salts that thermally decompose in the presence of catalytic amounts of copper compounds, N-allyloxypyridinium salts that can be thermally converted to acidic species in the presence of 2,2'-azobutyronitrile or benzoyl peroxide. The initiators will be present in any effective amount to initiate the cationic cure process, and customarily will be present in amounts of 0.1 to 10% by weight of the composition.

The preferred hydroxyl-containing compounds are diols, such as, polycaprolactone diols (e.g. the diol sold under the tradename Tone 0201, a product of Union Carbide); polyester diols (e.g. the diol sold under the tradename Rucoflex S-107-210, a product of Ruco Polymer Corporation); bisphenol A based polyether diols (e.g. the diol sold under the tradename Syn Fac 8031, a product of Milliken Chemicals); aliphatic diols (e.g. the diol sold under the tradename MP-diol, a product of Arco Chemical Company); aromatic polyester diols (e.g. the diol sold under the tradename Stepanpol, a product of Stepan Company). When used, the alcohol or polyol commonly will be present in a molar ratio of the hydroxyl functionality to the epoxide functionality in a range of 1:10 to 10:1, although any effective ratio to obtain the desired end use properties can be used.

In some end use adhesive or coating applications, the compositions may contain inert or electrically or thermally conductive fillers. The weight percentages and choice of filler for various end use applications will be known to those skilled in the art. Examples of such fillers are carbon, silica, alumina, silver, copper, gold, nickel, aluminum nitride, boron nitride, and silicon carbide. Typically, such fillers will be present in amounts ranging up to about 95% by weight of the composition.

In another embodiment this invention relates to visible-light initiated cationically-curable compositions containing epoxides. The capability of having the curing mechanism for the styrene oxide moieties initiated by visible light permits formulations that may contain polyurethanes.

Poly(urethane) polymers are used in adhesive and coating applications wherever the application requires abrasion resistance, skin flexibility, fast curing, good adhesion and chemical resistance. The urethane (or carbamate) group can be both a good hydrogen-bond donor and a good hydrogen-bond acceptor. Polyurethanes, however, have not been used in compositions that are intended to be cationically cured.

When urethanes are exposed to UV radiation, one process that may occur is absorption of the radiation energy by the urethane functionality followed by degradation to an amine, which is a Lewis base. A Lewis base is a substance that can furnish an electron pair to form a covalent bond. Since the cationic polymerization of the epoxy functionality occurs upon the liberation of an acidic species from the photoinitiator when it is exposed to actinic radiation, any compound that would quench the acid generated from the photoinitiator would hinder the cationic polymerization of the epoxy. A Lewis base with sufficient reactivity to furnish an electron pair to the acid generated by the photoinitiator, would quench the acid and inhibit the polymerization. Thus, Lewis bases, such as amines and hydroxide or alkoxide anions would have sufficient reactivity to quench the active acidic species, although epoxides and ethers would not. For this reason, it has not been practical in the past to form a composition of both cationically curable epoxides and urethanes to take advantage of the properties of both these compounds.

It has now been discovered that the styrene oxide containing compounds of this invention have sufficient reactivity to polymerize under visible light-initiated cationically cure conditions, in contrast to the cycloaliphatic oxides. Urethanes will not degrade significantly in the presence of visible light; therefore, it is possible to formulate compositions that contain both epoxide and urethane functionalities.

Photosensitizers are compounds known and used in the art to shift the wavelength of light required for a subsequent photoinitiation event, such as the response of onium salts, to longer wavelengths. The photosensitizers absorb actinic radiation energy and are promoted to an excited state. Direct electron transfer from excited-state photosensitizers to the photoinitiator onium salts yields photosensitizer radical cations. These may initiate cationic polymerization by themselves, or serve as precursors of cationic initiators. Indirect electron transfer processes are also known, in which photosensitizers undergo homolytic bond cleavage or H-abstraction from donors to yield free radicals, which are oxidized to cationic photoinitiators by electron transfer to onium salts. Therefore, cationic photoinitiators can be made active when exposed to long wavelength radiation, i.e. near-UV or visible-light when used in combination with photosensitizers. Suitable photosensitizers include, but are not limited to, anthracene, perylene, phenothiazine, thioxanthone and derivatives, benzophenone, coumarin and derivatives, and 9-anthracenemethanol. The preferred photosensitizers are anthracene and 9-anthracenemethanol; more preferred is the 9-anthracene-methanol, which itself can become covalently bound to the polymer network. The photosensitizers are used in amounts that range from 0.1 to 10 weight percent.

EXAMPLE 1

Preparation of 1,3-diisopropenylbenzene Dioxide

A suspension of 1 equivalent of 1,3-diispropenyl benzene (5 mL, 0.925 g/mL, 29.2 mmol) and 6 equivalents of sodium bicarbonate (15.9 g, 190 mmol) in a 2:1 mixture (volume:volume) of acetone:water (total 450 mL) was treated with an aqueous solution containing 2 equivalents of potassium persulfate (Oxone®) (36.5 g, 59.3 mmol). The suspension was stirred at room temperature for 3 hours. The pH was monitored during this time and remained neutral. The mixture was then vacuum filtered with a Buechner funnel and the residual solids washed with methylene chloride (150 mL). The biphasic filtrates were partitioned, and the aqueous phase was extracted with methylene chloride (2×200 mL). The organics were combined, washed with deionized water (200 mL), and dried over anhydrous $NaHCO_3$. The solvents were removed in vacuo at 35° C. A total of 4.83 g of clear oil was obtained as the product, confirmed by $^1H$ NMR. An IR indicated no hydroxyls. After 13 days at room temperature, no advancement of the epoxide was observed.

EXAMPLE 2

Preparation of Divinylbenzene Dioxide

Using divinyl-benzene as the starting material and the same procedure as in Example 1, 4.92 g of product as a mixture of isomers, confirmed by ¹H NMR, was obtained. After one year at room temperature, no advancement was observed.

EXAMPLE 3

UV Formulations

In order to demonstrate suitability for UV-curing, the epoxide monomer of Example 1 was formulated into adhesive compositions with various diols and, as the photoinitiator, 1% by weight of a 50% by weight solution of an arylsulfonium salt in propylene carbonate, sold under the tradename UVI-6974 by Union Carbide. These compositions were compared to control formulations containing a cycloaliphatic epoxide obtained from Union Carbide, as product ERL-4221, which has the structure:

A sample in the range of 1.5 to 3.0 mg for each composition was exposed to UV radiation and the rate of cure followed by a DPA-7 Perkin-Elmer Photo-Differential Scanning Calorimeter (P-DSC). Each sample was equilibrated to constant temperature (25° C.) on the Calorimeter for one minute and then exposed to irradiation for a total of four minutes using a 100 Watt Mercury short arc lamp. The resultant traces showed an exotherm represented as a sharp or broad peak. The diol used in the compositions, the molar ratio of epoxy to diol, and the DSC results are set out in Table 1 for the inventive styrene epoxy, and in Table 2 for the cycloaliphatic epoxy. In the Tables, $T_{max}$ is the time it took to reach the peak maximum exotherm in seconds, and $\Delta H$ is the exotherm of the reaction in kJoules per mole of epoxy, measured as the area over the curve from the four minute baseline back to the onset of exotherm.

The time the reaction takes to reach $T_{max}$ is a direct indication of the speed of the reaction; thus, the shorter the time (i.e. the sharper the peak), the faster the cure reaction for the epoxy, which is a desirable property for these adhesive compositions. In the following tables, the peaks are designated either sharp or broad; for purposes herein, if more than half the exotherm occurred in the first 30 seconds, the peak was defined as sharp, and conversely, if less than half the exotherm occurred in the first 30 seconds, the peak was defined as broad.

The $\Delta H$ values are a direct indication of the degree of epoxy ring opening, with the more negative numbers reflecting the higher degree of conversion of the epoxy.

The results indicate that the styrene compositions cure more quickly and more fully than cycloaliphatics, and that they are more compatible with a broader range of diols and at varying molar ratios than the cycloaliphatics. Referring to the data in Tables 1 and 2, it can be seen that the rates of cure ($T_{max}$) extend from 2.94 seconds to 6.12 seconds for the styrene epoxy, and from 4.62 seconds to 42.66 seconds for the cycloaliphatic epoxy, and that the extents of cure range from -79.1 kJ to -56.4 kJ for the styrene epoxy, and from -79.4 to -10.0 kJ for the cycloaliphatic epoxy. These ranges show that the rates of cure and extents of cure for the formulations containing the styrene epoxy were less affected by the choice of diol and the ratio of epoxide to diol than were the formulations containing the cycloaliphatic epoxy.

The diols that were used in the formulations are designated in the Tables by their tradenames. The diol sold under the tradename Tone 0201 is a product of Union Carbide and is a polycaprolactone diol. The diol sold under the tradename Rucoflex S-107-210 is a product of Ruco Polymer Corporation and is a polyester diol. The diol sold under the tradename Syn Fac 8031 is a product of Milliken Chemicals and is a bisphenol A based polyether diol. The diol sold under the tradename MP-diol is a product of Arco Chemical Company and is an aliphatic diol. The diol sold under the tradename Stepanpol is a product of Stepan Company and is an aromatic polyester diol.

TABLE 1

DSC Data for Inventive Epoxy of Example 1

| DIOL | Molar Ratio Epoxy:Diol | $T_{max}$** seconds | $\Delta H$ kJ/mole epoxide |
|---|---|---|---|
| none | | 3.84 | -57.8 |
| Rucoflex 107 | 1:1 | 4.32 | -84.1 |
| Rucoflex 107 | 3:1 | 4.20 | -79.1 |
| SynFax 8031 | 1:1 | 4.74 | -71.8 |
| SynFac 8031 | 3:1 | 3.57 | -65.5 |
| StepanoL PS-4002 | 1:1 | 6.12 | -76.0 |
| Stepanol PS-4002 | 3:1 | 4.83 | -62.6 |
| MP-dioL* | 1:1 | 4.35 | -77.4 |
| MP-dioL* | 3:1 | 2.94 | -58.2 |
| Tone 0201 | 1:1 | 3.57 | -73.4 |
| Tone 0201 | 3:1 | 3.96 | -56.4 |
| Tone 0201 | 1:3 | 4.59 | -75.9 |

Notes on Table 1:
* Insolubie in formulation.
** All peaks are sharp.

TABLE 2

DSC Data for Comparative Epoxy ERL-4221

| DIOL | Molar Ratio Epoxy:Diol | $T_{max}$ seconds | $\Delta H$ kJ/mole epoxide |
|---|---|---|---|
| none | — | 4.62 sharp | -10.0 |
| Rucoflex 107 | 1:1 | 6.81 sharp | -68.9 |
| Rucoflex 107 | 3:1 | 2.10 sharp | -42.9 |
| SynFac 8031 | 1:1 | 13.47 broad | -67.8 |
| SynFac 8031 | 3:1 | 13.17 broad | -39.7 |
| Stepanol PS-4002 | 1:1 | 17.10 broad | -79.4 |
| Stepanol PS-4002 | 3:1 | 5.34 sharp | -14.3 |
| MP-diol | 1:1 | 21.20 broad | -78.4 |
| MP-diol | 3:1 | 6.39 sharp | -49.0 |
| Tone 0201 | 1:1 | 9.21 broad | -62.0 |
| Tone 0201 | 3:1 | 6.00 sharp | -30.3 |
| Tone 0201 | 1:3 | 42.66 broad | -44.0 |

EXAMPLE 4

Accelerators for UV-Curable Compositions

This example illustrates that small amounts of a styrene oxide can accelerate the curing rates of epoxides that exhibit moderate rates of UV-cure, for example, glycidyl epoxides.

A composition, designated composition A, was prepared to contain: 1) one equivalent of epoxide functionality from a glycidyl tris-epoxide sold under the tradename Heloxy 44® by Shell Chemical, Houston, Tex.; 2) one equivalent of hydroxyl functionality from 2-methyl-1,3-propanediol, sold under the tradename MP diol from Arco; and; 3) 2% by weight of arylsulfonium salt, sold under the tradename UVI-6974 by Union Carbide. The cure rate of this composition was analyzed by P-DSC.

To this composition A was added 25% by weight of divinylbenzene dioxide (prepared from example 2); this composition was designated composition B. The rate and extent of cure were analyzed by P-DSC and showed significant increases over the rate and extent of cure of composition A.

Figure 1:
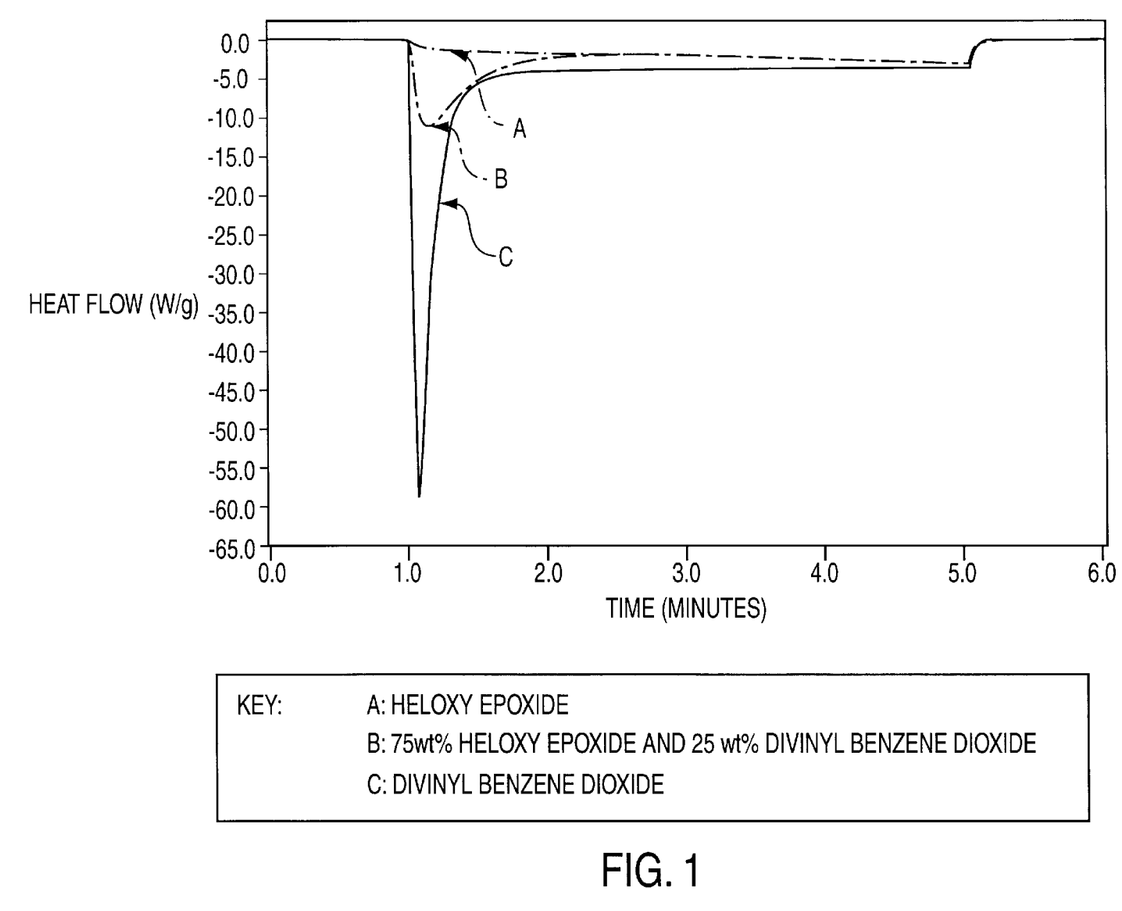
FIG. 1 is a trace of DSC curves for three compositions: composition A contains Heloxy epoxide; composition B contains 25% by weight divinylbenzene dioxide in combination with 75% by weight Heloxy epoxide; and composition C contains divinylbenzene dioxide.

The DSC curves of compositions A and B, and that of a comparative composition containing divinylbenzene dioxide, designated composition C, are shown in FIG. 1. As is understood by those skilled in the art, the peak on a DSC curve represents the exotherm; the sharper the peak, the faster the exotherm has occurred. FIG. 1 shows that composition C exhibits the sharpest peak. Composition A, which contains only the Heloxy epoxide, exhibits a very shallow peak, which is interpreted as the composition having almost no reactivity, and very slow cure. Composition B, which contains the 25% by weight divinylbenzene dioxide in combination with 75% by weight Heloxy epoxide, exhibits a fast exotherm (although broader than that of composition C), followed by a fast return to a constant baseline. This is interpreted to show a co-reaction between the Heloxy epoxide and the divinylbenzene dioxide, in contrast to a long, broad exotherm, which would be indicative of a summation of the Heloxy epoxide and the divinylbenzene reacting independently.

EXAMPLE 5

Preparation of Additional Styrene Oxides

Using the same procedure as in Example 1, the following epoxides were prepared from the corresponding starting materials as listed in Table 3. The products were confirmed by $^1$H NMR.

TABLE 3

Additional Styrene Oxides

| STARTING MATERIAL | EPOXIDE |
| --- | --- |
| beta-methyl styrene | beta-methyl styrene mono-epoxide |
| cinnamyl acetate | cinnamyl acetate epoxide |
| cinnamyl methyl ether | cinnamyl methyl ether epoxide |
| isoeugenol methyl ether mix of isomers | isoeugenol methyl ether epoxide mix of isomers |
| isoeugenol acetate | isoeugenol acetate epoxide |

EXAMPLE 6

Photo-Differential Scanning Calorimetric Analysis

Photo-DSC of various styrene oxides was conducted by formulating the epoxides with a photoinitiator and a diol. The specific formulation of styrene oxide, diol, molar ratio of epoxide to hydroxyl functionality, $T_{max}$, and the kJ per mole of epoxy are set out in the following Table 4:

TABLE 4

| MONOMER | DIOL | Molar ratio Epoxy:Diol | $T_{MAX}$ | ΔH kJ/Mole EPOXIDE |
| --- | --- | --- | --- | --- |
| 1. alpha-methyl styrene bis epoxy | — | — | 3.84 | −57.8 |
| 2. alpha methyl styrene epoxy | — | — | 3.60 | −53.3 |
| 3. alpha methyl styrene epoxy | MP-diol* | 1:1 | 3.12 | −80.9 |
| 4. alpha methyl styrene epoxy | MP-diol* | 3:1 | 2.88 | −56.4 |

TABLE 4-continued

| MONOMER | DIOL | Molar ratio Epoxy:Diol | $T_{MAX}$ | ΔH kJ/Mole EPOXIDE |
| --- | --- | --- | --- | --- |
| 5. alpha methyl styrene bis epoxy | Tone polyol | 1:1 | 3.57 | −72.8 |
| 6. alpha methyl styrene epoxy | Tone polyol | 1:1 | 3.78 | −76.5 |
| 7. alpha methyl styrene epoxy | Tone polyol | 3:1 | 3.30 | −66.7 |
| 8. beta-methyl styrene epoxy | — | — | 4.62 | −85.4 |
| 9. beta-methyl styrene epoxy | MP-diol* | 1:1 | 5.28 | −102.6 |
| 10. beta-methyl styrene epoxy | MP-diol* | 3:1 | 4.98 | −75.7 |
| 11. beta-methyl styrene epoxy | Tone polyol | 1:1 | 8.28 | −80.5 |
| 12. beta-methyl styrene epoxy | Tone polyol | 3:1 | 6.24 | −54.5 |
| 13. cinnamyl acetate epoxy | — | — | 0 | 0 |
| 14. cinnamyl acetate epoxy | MP-diol* | 1:1 | 8.76 | −27.5 |
| 15. cinnamyl acetate epoxy | MP-diol* | 3:1 | 8.58 | −16.1 |
| 16. cinnamyl acetate epoxy | Tone polyol | 1:1 | 11.22 | −55.6 |
| 17. cinnamyl acetate epoxy | Tone polyol | 3:1 | 10.23 | −30.8 |
| 18. isoeugenol acetate epoxy | — | — | 23.1 | −15.7 |
| 19. isoeugenol acetate epoxy | MP-diol | 1:1 | 7.17 | −70.1 |
| 20. isoeugenol acetate epoxy | MP-diol | 3:1 | 7.50 | −67.6 |
| 21. isoeugenol acetate epoxy | Tone polyol | 1:1 | 8.76 | −75.0 |
| 22. isoeugenol acetate epoxy | Tone polyol | 3:1 | 9.39 | −65.0 |
| 23. cinnamyl methyl ether epoxy | — | — | 7.38 | −43.9 |
| 24. cinnamyl methyl ether epoxy | MP-diol* | 1:1 | 14.46 | −57.8 |
| 25. cinnamyl methyl ether epoxy | MP-diol* | 3:1 | 13.65 | −63.6 |
| 26. cinnamyl methyl ether epoxy | Tone polyol | 1:1 | 3.18 | −98.8 |
| 27. cinnamyl methyl ether epoxy | Tone polyol | 3:1 | 2.40 | −82.4 |

* Insoluble in formulation

The P-DSC data give information that is useful in understanding the capabilities of these monomers in the formulation of cationically-curable adhesives:

The reactivity (per epoxide ring) for the difunctional alpha-methyl styrene bis-epoxide and that of the monofunctional alpha-methyl styrene epoxide are comparable (cf. entries 1 & 2, and 5 & 6);

The substitution pattern of the epoxide has an impact on its reactivity. Comparison of $T_{(max)}$ for α- and β-methyl styrene oxide formulations indicate that the α-isomer reacts faster than the β-isomer under similar conditions (cf. entries 2 & 8; 3 & 9; 4 & 10; 6 & 11; 7 & 12). This can be attributed to the fact that the α-isomer can ring open to a more stable tertiary, benzylic carbocation, while the β-isomer affords a less stable secondary, benzylic carbocation. Comparison of the enthalpies of the polymerization (ΔH's) indicates that the β-isomer appears to react as much or more completely (cf. entries 2 & 8; 3 & 9; 4 & 10; 6 & 11; 7 & 12).

With respect to the cinnamyl derivatives, entry 13 demonstrates that in the absence of an alcohol, the ester group appears to mitigate the reactivity of the epoxide, and cinnamyl acetate epoxide does not polymerize. Comparison of the cinnamyl acetate epoxide formulations (entries 13–17) with the corresponding cinnamyl ether epoxide formulations (entries 23–27) shows faster and more complete reaction for the cinnamyl ether epoxide formulations. During cure, the ester carbonyl presumably interacts with the proximal cationic center formed upon ring opening, thereby inhibiting the propagation reaction.

In contrast to the cinnamyl acetate epoxide, the isoeugenol acetate epoxide does cure in the absence of a blending alcohol (cf. entries 13 and 18). This effect can be attributed to two structural features of the epoxide. First, the ester carbonyl is further removed from the nascent carbocationic site at the benzylic position. Second, the aromatic ring is not sufficiently flexible to allow interaction between these sites. These two features serve to mitigate "communication" between the carbonyl and the epoxide. Moreover, the isoeugenol acetate epoxide is relatively reactive in the presence of alcohols (entries 19–22). These results indicate that an ester functionality can be tolerated in these styrene oxide systems.

EXAMPLE 7

Visible Light-Initiated Cure

The commercial product ERL-4221 (see Example 3, Table 2) and a styrene oxide moiety containing compound (1,3-diisopropenylbenzene dioxide) were formulated into canonically curable adhesive compositions containing a photosensitizer and irradiated with visible light. The styrene oxide has the structural formula The adhesive formulation containing the styrene oxide moiety containing compound was as follows:

| Composition 7A *: | |
|---|---|
| Diisopropenylbenzene dioxide | 2.0355 g |
| Poly(caprolactone) diol (Union Carbide Corp., Tone 0201 ®) | 1.5082 g |
| Arylsulfonium salt, photoinitiator Union Carbide Corp., UVI-6974 | 0.1821 g |
| Anthracene * in visible light curable composition | 0.0084 g |

* The composition was held in a brown vial to keep from light.

The adhesive formulation containing the ERL-4221 containing compound was as follows:

| Composition 7B *: | |
|---|---|
| ERL-4221 cycloaliphatic epoxy | 1.6705 g |
| Poly(caprolactone) diol (Union Carbide Corp., Tone 0201 ®) | 0.9514 g |
| Arylsulfonium salt, photoinitiator Union Carbide Corp., UVI-6974 | 0.1361 g |
| Anthracene * in visible light curable composition | 0.0074 g |

The components for each of the formulations were protected from light and heated at about 60° C. while stirring until each mixture became homogeneous.

A drop of each composition was placed on a microscope slide and exposed to visible light from a Luxor® light source (sold by Ablestik Laboratories, California) at 400 to 570 nm for 30 seconds at ambient conditions.

The sample containing the ERL-4221 cycloaliphatic epoxide exhibited a light surface cure with no cure underneath the surface.

The sample containing the diisopropenylbenzene cured to a tacky rubbery gel immediately after irradiation, and a hard rubbery gel 30 minutes after irradiation and under ambient conditions.

EXAMPLE 8

Urethane Containing Compositions

Compositions 7A and 7B were formulated with 5–10% by weight of model urethane compounds and one poly (urethane) and cured with visible light as in the previous Examples. These formulations suggest that poly(urethanes) with analogous structures to the model compounds can be used in these formulations.

Table 5 sets out the model urethane compound and amounts of the urethanes and compositions 7A and 7B used in the formulations and the curing results.

TABLE 5

| Urethane | | Composition | | Cure Result |
|---|---|---|---|---|
| | | 7A | 0.2092 g | Cured to soft |
| | | urethane | 0.0165 g | rubbery gel |
| | | 7B | 0.0189 g | No cure |
| | | urethane | 0.2019 g | |

TABLE 5-continued

| Urethane | Composition | | Cure Result |
|---|---|---|---|
| Ethyl N-ethylcarbamate (ethyl carbamate with N-ethyl group) | 7A urethane 7B urethane | 0.2090 g 0.0112 g 0.2153 g 0.2010 g | Cured to soft rubbery gel No cure |
| Ethyl N,N-diphenylcarbamate | 7A urethane 7B urethane | 0.2422 g 0.0138 g 0.2200 g 0.0187 g | Cured to soft rubbery gel No cure |
| Ethyl N-methyl-N-phenylcarbamate | 7A urethane 7B urethane | 0.2099 g 0.0215 g 0.2168 g 0.0232 g | Cured to soft rubbery gel No cure |

The data indicate that the cycloaliphatic epoxy will not cure when the cure is initiated with visible light, and that the diisopropenylbenzene dioxide will cure in the presence of a urethane compound when the cure is initiated with visible light.

EXAMPLE 9

Polyurethane Containing Composition

A composition containing a polyurethane diol, sold under the tradename K-Flex by King Industries, was prepared and cured with visible light as in the preceding examples. In this example, 9-anthracenemethanol was used as the photosensitizer.

| Composition 9A: | |
|---|---|
| Diisopropenylbenzene dioxide | 2.0051 g |
| Poly(caproiactone) diol (Union Carbide Corp., Tone 0201 ®) | 1.4859 g |
| Arylsulfonium salt, photoinitiator Union Carbide Corp., UVI-6974 | 0.1847 g |
| 9-Anthracenemethanol | 0.0090 g |

These materials were combined in a brown vial and gently stirred until homogeneous. A portion of this mixture (0.3239 g) was transferred to a brown glass bottle, and K-Flex polyurethane diol (0.285 g) was added. The mixture was stirred until homogeneous, and then exposed to Luxor visible light for 30 sec. Both the original mixture, and the mixture containing K-flex immediately cured to form a rubbery gel.

EXAMPLE 10

Polyurethane Containing Composition

A composition containing a polyurethane diol, sold under the tradename K-Flex by King Industries, was prepared and cured with visible light as in the preceding examples. In this example, anthracene was used as the photosensitizer.

| Composition 10A: | |
|---|---|
| Diisopropenylbenzene dioxide | 2.0142 g |
| Poly(caprolactone) diol (Union Carbide Corp., Tone 0201 ®) | 1.4858 g |
| Arylsulfonium salt, photoinitiator Union Carbide Corp., UVI-6974 | 0.1806 g |
| Anthracene | 0.0091 g |

These materials were combined in a brown vial and gently stirred until homogeneous. A portion of this mixture (0.4554 g) was transferred to a brown glass bottle, and K-Flex polyurethane diol (0.0239 g) was added. The mixture was stirred until homogeneous, and then exposed to Luxor visible light for 30 sec. Both the original mixture, and the mixture containing K-flex immediately cured to form a rubbery gel.

EXAMPLE 11

Adhesive Formulation and Performance

Diisopropenylbenzene dioxide was formulated into an adhesive composition and its performance compared to a similar composition containing a cycloaliphatic epoxy. The compositions are given here:

| Composition 11A: | |
|---|---|
| Diisopropenylbenzene dioxide | 24.3 wt % |
| Bispheriol A diglycidyl ether (Epon 828, Shell Chemical) | 48.5 |
| Flexible epoxy (Epon 872, Shell Chemical) | 24.3 |
| Triarylsulfonium hexafluoroantimonate | 1.9 |
| Glycidyitriethoxysilane (A187, Witco) | 0.48 |

-continued

| Composition 11A: | |
|---|---|
| Surfactant (Modaflow, Monsanto) | 0.48 |

| Composition 11B: | |
|---|---|
| Cycloaliphatic epoxy (Ciba-Geigy, CY 179) | 24.3 wt % |
| Bisphenol A diglycidyl ether (Epon 828, Shell Chemical) | 48.5 |
| Flexible epoxy (Epon 872, Shell Chemical) | 24.3 |
| Triarylsulfonium hexafluoroantimonate | 1.9 |
| Glycidyltriethoxysilane (A187, Witco) | 0.48 |
| Surfactant (Modaflow, Monsanto) | 0.48 |

For each of the tests below the compositions were cured with a Fusion Systems UV Lamp using a D bulb with the samples passing under the lamp at 1.21 meter (4 feet) per minute These compositions were tested for Lap Shear Strength Versus Temperature using ASTM D 1002 test method with the results given in Table 6.

TABLE 6

| | Lap Shear Strength | | | | |
|---|---|---|---|---|---|
| | −20° F. −29° C. | 75° F. 24° C. | 180° F. 82° C. | 250° F. 120° C. | 325° F. 160° C. |
| 11A | 1600 psi 11 MPa | 2120 psi 14.6 MPa | 1800 psi 12 MPa | 1350 psi 9.30 MPa | 1010 psi 6.96 MPa |
| 11B | 1440 psi 9.92 MPa | 1720 psi 11.9 MPa | 1530 psi 10.5 MPa | 970 psi 6.7 MPa | 660 psi 4.6 MPa |

The compositions were used to seal a cavity in a glass filled nylon substrate. The test assemblies were placed in ovens and tested for the time to failure at elevated temperature. The samples were stored in an oven for 14 days at temperatures of 350° F. and 400° F. The results are set out in Table 7.

TABLE 7

| | Elevated Temperature Performance | |
|---|---|---|
| | 350° F. | 400° F. |
| 11A | no failure | no failure |
| 11B | no failure | failure at 8 days |

The compositions were tested for solvent resistance when used to bond glass to a cold rolled metal substrate. The assemblies were held in solvent until bond failure was observed, or until 14 days duration.

TABLE 8

| | Solvent Resistance | | | |
|---|---|---|---|---|
| | Water | Methylene Chloride | Toluene | Acetone |
| 11A | no failure | no failure | no failure | no failure |
| 11B | 10 days | 4 days | 10 days | 7 days |

The data show that the use of the diisopropenylbenzene dioxide provides a UV curable epoxy formulation with significantly increased thermal and chemical resistance over the cycloaliphatic epoxy containing composition.

What is claimed is:

1. A cationically-curable adhesive or coating composition comprising (a) a radiation- or thermally-initiated cationically-curable compound having the structure in which $R^1$ to $R^4$ independently represent hydrogen, or aliphatic, alicyclic or aromatic groups, which may contain heteroatoms, characterized in that they do not hinder the cationic polymerization of the epoxy functionality either through steric interaction or through the action of a Lewis base; y is an integer 1–6, w is an integer 0–5, provided that $y+w \leq 6$; and (b) a cationic photo- or thermal-initiator; and (c) one or more alcohols or polyols.

2. The cationically-curable adhesive or coating composition according to claim 1 in which cationic cure is initiated with visible light and the composition further comprises a photosensitizer.

3. The cationically-curable adhesive or coating composition according to claim 2 further comprising one or more urethanes or polyurethanes.

4. The cationically-curable adhesive or coating composition according to claim 2 or 3 in which the photosensitizer is 9-anthracenemethanol.

* * * * *